United States Patent [19]

Tanemura et al.

[11] 4,092,426
[45] May 30, 1978

[54] NOVEL AMINOBENZOIC ACID DERIVATIVES, PROCESS FOR PREPARING THE SAME AND PHARMACEUTICAL COMPOSITION CONTAINING THE SAME

[75] Inventors: Mitsuru Tanemura, Tokyo; Teizo Shinozaki, Matsudo; Minoru Shindo, Kurume; Shun-ichi Hata, Yokohama; Koji Mizuno; Masayoshi Ono, both of Tokorozawa; Kiyoshige Wakabayashi, Ohmiya; Toshiaki Nakano, Tokyo; Yasuho Nishii, Niiza; Takashi Matsuno, Ohmiya; Yoshiyuki Ohsugi, Kodaira, all of Japan

[73] Assignee: Chugai Seiyaku Kabushiki Kaisha, Tokyo, Japan

[21] Appl. No.: 691,432

[22] Filed: June 1, 1976

[30] Foreign Application Priority Data

June 11, 1975 Germany .............................. 2526092
Apr. 12, 1976 Japan .................... 51-41041

[51] Int. Cl.² .................... A01N 9/20; C07C 63/33
[52] U.S. Cl. .................... 424/309; 260/518 A; 260/518 R
[58] Field of Search .................... 260/518 R, 518 A; 424/309

[56] References Cited

U.S. PATENT DOCUMENTS

| | | | |
|---|---|---|---|
| 3,313,848 | 4/1967 | Scherrer et al. | 260/518 A |
| 3,369,042 | 2/1968 | Scherrer | 260/518 R |
| 3,390,172 | 6/1968 | Scherrer | 260/518 R |
| 3,511,873 | 5/1970 | Picciola | 260/518 R |
| 3,989,746 | 11/1976 | Nohara et al. | 260/518 R |

OTHER PUBLICATIONS

Kodama et al., Chem. Abst., vol. 83, pp. 417, #192845n, (1975).
Sota et al., Yakugaku Zasshi, vol. 89, pp. 1392-1400, (1969).
Frumina et al., Chem. Abst., vol. 72, pp. 481, #19317v (1972).

*Primary Examiner*—James O. Thomas, Jr.
*Assistant Examiner*—James H. Reamer
*Attorney, Agent, or Firm*—Browdy and Neimark

[57] ABSTRACT

An aminobenzoic acid derivative represented by the formula

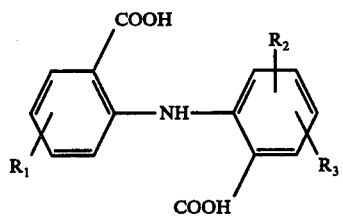

wherein $R_1$, $R_2$ and $R_3$ are defined hereinbelow, which has excellent activity for improving liver function and for potentiating and normalizing immunity; a process for preparing the same; and a pharmaceutical composition containing the same are disclosed.

22 Claims, 8 Drawing Figures

NOVEL AMINOBENZOIC ACID DERIVATIVES, PROCESS FOR PREPARING THE SAME AND PHARMACEUTICAL COMPOSITION CONTAINING THE SAME

This invention relates to a novel aminobenzoic acid derivative, a process for preparing the same and a pharmaceutical composition containing the same.

The aminobenzoic acid derivative according to this invention is represented by the formula

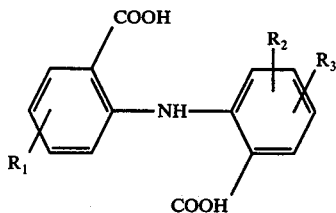

wherein $R_1$ is a hydrogen atom or a halogen atom and $R_2$ and $R_3$ are independently a hydrogen atom, a halogen atom or an alkyl radical having 1 – 6 carbon atoms, provided that $R_1$, $R_2$ and $R_3$ are not simultaneously hydrogen atoms.

All the aminobenzoic acid derivatives according to this invention are novel. Since the derivatibes have excellent activity for improving liver function and for potentiating and normalizing immunity, and antiviral activity, they are useful as a liver function improving agent and a medicine for treating a disease from immune depletion, such as rheumatic arthritis, autoimmune diseases, antitumor activity against transplanted tumor cells (Sarcoma-180), bacterial infectious diseases and asthma.

Examples of the derivatives represented by formula (I) are:
N-2'-carboxy-4'-chlorophenylanthranilic acid,
N-2'-carboxy-4'-bromophenylanthranilic acid,
N-2'-carboxy-4'-methylphenylanthranilic acid,
N-2'-carboxy-4'-ethylphenylanthranilic acid,
N-2'-carboxy-4'-butylphenylanthranilic acid,
N-2'-carboxy-4'-chlorophenyl-4-chloroanthranilic acid,
N-2'-carboxyphenyl-4-chloroanthranilic acid,
N-2'-carboxy-4'-methylphenyl-4-chloroanthranilic acid,
N-2'-carboxy-4'-ethylphenyl-4-chloroanthranilic acid,
N-2'-carboxy-4'-propylphenyl-4-chloroanthranilic acid,
N-2'-carboxy-4'-butylphenyl-4-chloroanthranilic acid,
N-2'-carboxyphenyl-4-bromoanthranilic acid,
N-2'-carboxy-4'-chlorophenyl-4-bromoanthranilic acid,
N-2'-carboxy-4'-chlorophenyl-5-chloroanthranilic acid,
N-2'-carboxy-5'-chlorophenyl-5-chloroanthranilic acid,
N-2'-carboxy-6'-methylphenylanthranilic acid,
N-2'-carboxy-6'-methylphenyl-4-chloroanthranilic acid,
N-2'-carboxy-5'-methylphenyl-4-chloroanthranilic acid,
N-2'-carboxy-3'-methylphenyl-4-chloroanthranilic acid,
N-2'-carboxy-3',6'-dimethylphenyl-4-chloroanthranilic acid,
N-2'-carboxy-5'-chloro-6'-methylphenylanthranilic acid, and
N-2'-carboxy-5'-chlorophenyl-4-chloroanthranilic acid.

The object compound represented by the formula (I) may be prepared by reacting a 2-halogenobenzoic acid derivative represented by the formula

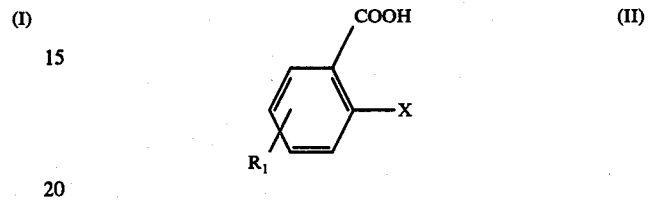

wherein $R_1$ is the same as defined above and X is a halogen atom with anthranilic acid or its derivative reresented by the formula

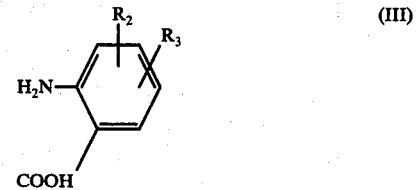

wherein $R_2$ and $R_3$ are the same as defined above, provided that $R_1$ of Formula (II), $R_2$ and $R_3$ are not simultaneously hydrogen atom.

The 2-halogenobenzoic acid derivatives (II) which may be used in this invention include, for example, 2-chlorobenzoic acid, 2,4-dichlorobenzoic acid, 2,4-dibromobenzoic acid and the like.

The anthranilic acid derivatives (III) which may be used in this invention as a starting compound include 4-chloroanthranilic acid, 5-chloroanthranilic acid, 4-chloro-3-methylanthranilic acid, 3-methylanthranilic acid, 5-methylanthranilic acid, 3,6-dimethylanthranilic acid and the like.

In accordance with this invention, the reaction of the 2-halogenobenzoic acid derivative (II) with anthranilic acid or its derivative (III) is carried out in a solvent at a temperature of more than 25° C, usually at a temperature of from 80° – 200° C for 1 – 10 hours and preferably, at a temperature of from 120° – 150° C for 3 – 5 hours.

The solvents useful in this invention include isoamyl alcohol, dimethylsulfoxide, dimethyl formamide, ethanol, butanol, n-amyl alcohol, diethylene glycol dimethylether, nitrobenzene, water and the like.

Anthranilic acid or its derivative (III) may be advantageously used in an excess amount, preferably 1.2 – 2.0 mole per mole of the 2-halogenobenzoic acid derivative. In order to carry out the reaction smoothly and to heighten the yield of the object product, an alkaline substance such as potassium carbonate, sodium carbonate or copper carbonate and metal or metal-containing compound such as powdery copper, cuprous chloride, cuprous bromide, cupric acetate and the like may be advantageously used as a reaction catalyst. It is preferable to use the alkaline substance in equivalent mole or more based on the total mole of compounds (II) and (III) whereas the metal or metal-containing compound is used in a very small amount. Furthermore, if a catalytic amount of iodine or an iodine-containing compound such as sodium iodide or cuprous iodide is used in addition to the catalyst exemplified above, the yield of the product will be significantly, increased.

The aminobenzoic acid derivative (I), the object product of this invention, may be converted to corresponding alkali salts such as sodium salts, potassium salts and the like in any conventional manner.

The aminobenzoic acid derivative (I), the object product of this invention may be formulated with an adjuvant as well as a pharmaceutically acceptable carrier into a pharmaceutical composition for improvement of liver function and a pharmaceutical composition for a disease from immune depletion suitable for oral administration, e.g. tablet, granule, powder, capsule filled with powder or granule, and the like or into parenteral injection which was dissolved in water. For the preparation of tablet, granule, powder or capsule, it is preferable to use, as a pharmaceutically acceptable carrier, lactose, starch, dextrin, sucrose, microcrystalline cellulose, kaolin, calcium carbonate, talc and the like, and for the parenteral injections it is preferable to dissolve the object compound in an aqueous solution isotonized with sodium chloride, potassium chloride and the like.

The aminobenzoic acid derivative (I) may be present in a pharmaceutical composition in an amount sufficient to exhibit the actions for improving liver function, and for potentiating and normalizing immunity. The dosage is usually 0.5 – 3000, preferably 10 – 300 mg body a day of the effective compound, when the composition is orally administered and it is usually 0.5 – 1000, preferably 1 – 100 mg body of the compound in case the composition is given as a parenteral injection.

Figure 1:
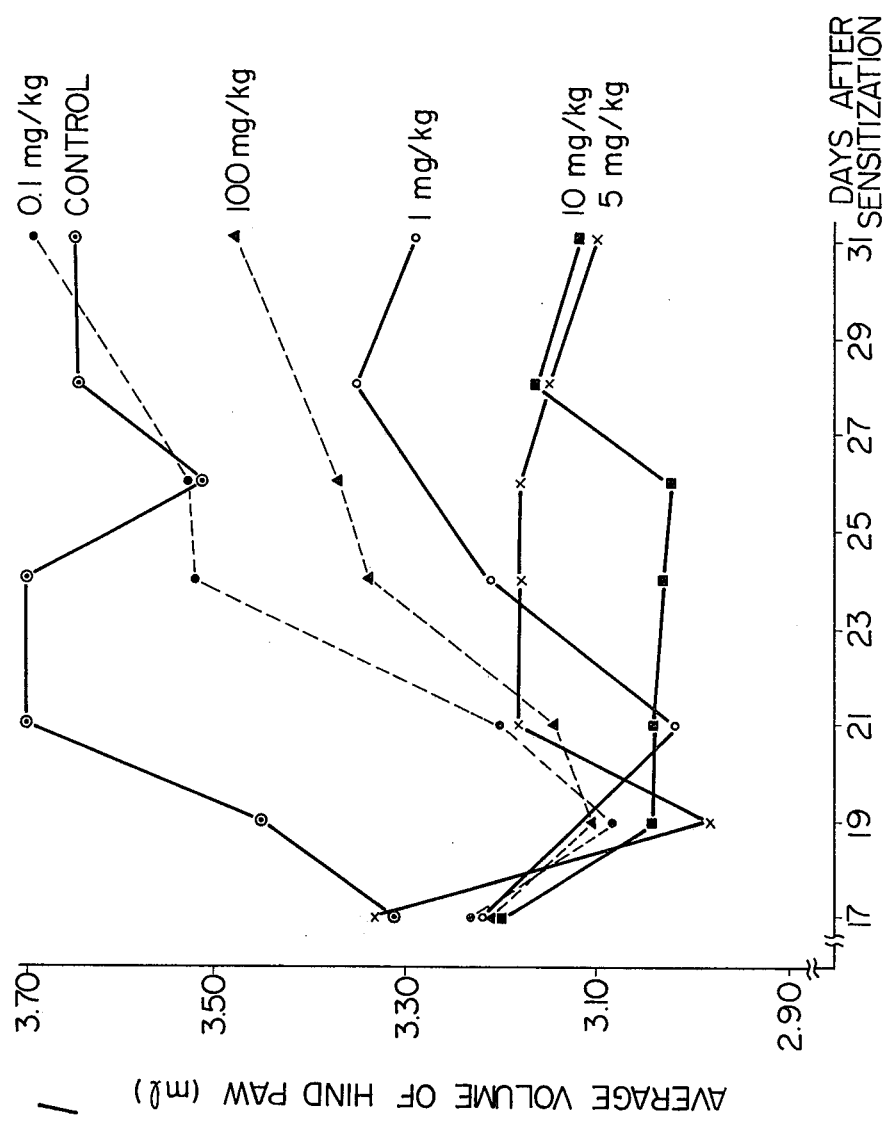
FIG. 1 is a graph showing the activity of the object compound according to this invention for treating adjuvant rheumatic arthritis.

In the graphs, the symbol ┼ means statistical standard deviation.

The present invention is further illustrated by the following Experiments and Examples, but they are not to be construed as limiting the scope of this invention.

EXPERIMENT 1

Action for decreasing triglyceride in liver

Sprague Dawley strain female rats each weighing 170 – 200 g which had been fasted for 15 hours were divided into groups of 4 rats each. The rats were orally administered a different test compound in a dose of 100 mg/kg, and 30 minutes after the administration, orally administered ethanol in a dose of 6 g/kg. Twenty-four hours after the administration of ethanol, the liver of each rat was taken out and neutral lipid level in the liver was measured in a conventional manner to calculate the ratio of preventing an increase in triglyceride content in the liver. For a control group, ethanol and, for the other control group, a glucose aqueous solution equivalent in calorific value to the same amount of ethanol were used and the same manner as those of test groups, and for the positive control group, commercially available 2-mercaptopropionylglycine was used instead of the test compound.

Table 1

| Test Compound | % Prevention* |
|---|---|
| N-2'-carboxyphenyl-4-chloroanthranilic acid | 67.1 |
| N-2'-carboxy-4-'-methylphenyl-4-chloroanthranilic acid | 53.2 |
| N-2'-carboxyphenyl-5-methylanthranilic acid | 20.1 |
| N-2'-carboxy-6'-methylphenyl-4-chloroanthranilic acid | 25.2 |
| N-2'-carboxy-5'-chlorophenyl-4-chloroanthranilic acid | 57.2 |
| N-2'-carboxy-3',6'-dimethylphenyl-4-chloroanthranilic acid | 45.8 |
| N-2'-carboxyphenyl-4-chloro-3-methylanthranilic acid | 40.5 |
| N-2'-carboxyphenyl-5-chloroanthranilic acid | 30.0 |
| sodium salt of N-2'-carboxyphenyl-4-chloroanthranilic acid | 63.6 |
| Control: 2-mercaptopropionylglycine | 9.3 |

*The % prevention was calculated by the following equation:

Percent Prevention =

$$\frac{\left(\begin{array}{c}\text{Amount of triglyceride}\\\text{in liver of the group}\\\text{administered ethanol}\end{array}\right) - \left(\begin{array}{c}\text{Amount of triglyceride in}\\\text{liver of the administered}\\\text{ethanol + test compound}\end{array}\right)}{\left(\begin{array}{c}\text{Amount of triglyceride}\\\text{in liver of the group}\\\text{administered ethanol}\end{array}\right) - \left(\begin{array}{c}\text{Amount of triglyceride in}\\\text{liver of the administered}\\\text{glucose}\end{array}\right)} \times 100$$

EXPERIMENT 2

Biliary Excretion Activity (a) Bromosulfophthalein (BSP) Test

Sprague Dawley strain female rats each weighing 150 – 190 g which had been fasted for 15 hours were divided into groups of 4 rats each. The rats were orally administered a different test compound in a dose of 100 mg/kg, and 60 minutes after the administration, each of the rats was injected through the tail vein with 28 mg/head of BSP. Thirty minutes after the injection, the blood of each rat was sampled from the heart and the concentration of BSP was determined in a conventional colorimetric manner. As control, a physiological saline solution was orally administered instead of the test compound.

The results are shown in Table 2.

Table 2

| Test Compound | % Remain of BSP |
|---|---|
| Control | 51.9±6.7 |
| N-2'-carboxyphenyl-4-chloro- | 17.3±8.4** (P<0.01) |

** Significant: Student's T-test based on the average value (b) Indocyanogree (ICG) Test Sprague Dawley strain male rats weighing 180 – 210 g which had been fasted for 15 hours were divided into groups of 4 rats each. The rats were orally administered a different test compound in a dose of 100 mg/kg, and 60 minutes after the administration, each of the rats was injected through the tail vein with 2 mg/head of ICG.

Fifteen minutes after the injection, the blood of each rat was sampled from the heart and the concentration of ICG in the blood was determined in a conventional colorimetric manner. As control, a physiological saline solution was used.

The results are shown in Table 3 below.

Table 3

| Test Compound | % Remain of ICG |
|---|---|
| Control (physiological saline solution) | 7.8 ± 1.5 |
| N-2'-carboxyphenyl-4-chloro-anthranilic acid | 5.1 ± 0.2** (P<0.02) |

**same as defined above (c) Bilirubin Excretion Activity

Sprague Dawley strain female rats each weighing 160 – 200 g which had been fasted for 15 hours were divided into groups of 6 rats each. The rats were orally administered with a different test compound in a dose of 100 mg/kg, and 60 minutes after the administration, each of the rats was injected through the tail vein with 150 g/head of bilirubin. Twenty minutes after the injection, the blood of each rat was sampled from the heart and the concentration of bilirubin in the blood was determined in a conventional manner.

As control, a physiological saline solution was used instead of the test compound. The results are shown in Table 4 below.

Table 4

| Test Compound | % Remain of Bilirubin |
|---|---|
| Control (physiological saline solution) | 85.4 ± 9.8 |
| N-2'-carboxyphenyl-4-chloro-anthranilic acid | 39.7 ± 13.3**(P<0.02) |

** same as defined above.

EXPERIMENT 3

Activity for Treating Adjuvant Arthritis (a Model Disease of Rheumatic Arthritis)

Sprague Dawley strain male rats (eight week old) were used as test animals. Adjuvant arthritis was revealed by subcutaneously injecting a suspension of killed tubercle bacillus in Freund's adjuvant in the tail of each rat. Seventeen days after the sensitization, degree of swelling of hind pawls of each rat was determined by measuring the volume of its hind paws and the rats were divided into groups of 10 members each so that average degree of swelling for each of the groups was approximately equal. Each group of rats was orally administered with the test compound, disodium salt of N-2'-carboxyphenyl-4-chloroanthranilic acid, in a dose as shown in Table 5 once a day for a week starting on the seventeenth day after the sensitization. Degree of swelling of hind paws of each rat was measured every second or third day after the completion of the administration of the test compound till the 31st day from the sensitization. The reduction in volume of the hind paws was used as an index to evaluate the pharmacological activity. The results are shown in FIG. 1. It was confirmed that the administration of the test compound in a dose of 5 or 10 mg/kg provides a significant level of activity for treating adjuvant arthritis of rat.

The results of the statistical test which was made on the values obtained on the 24th and 31st days from the sensitization are shown in Table 5.

Table 5

| Dose (mg/kg) | Day after the sensitization 24 | 31 |
|---|---|---|
| Control | 3.693 ± 0.130 (ml) | 3.646 ± 0.170 (ml) |
| 0.1 | 3.524 ± 0.170 | 3.762 ± 0.216 |
| 1 | 3.214 ± 0.161 | 3.289 ± 0.223 |
| 5 | 3.175 ± 0.100** | 3.102 ± 0.141* |
| 10 | 3.027 ± 0.126** | 3.121 ± 0.176* |
| 100 | 3.350 ± 0.168 | 3.482 ± 0.170 |

*Significant: Student's T-test (P<0.05) based on the average value
**Significant: Student's T-test (P<0.01) based on the average value

EXPERIMENT 4

Activity for Treating a Model of Autoimmune Disease

Figure 2:
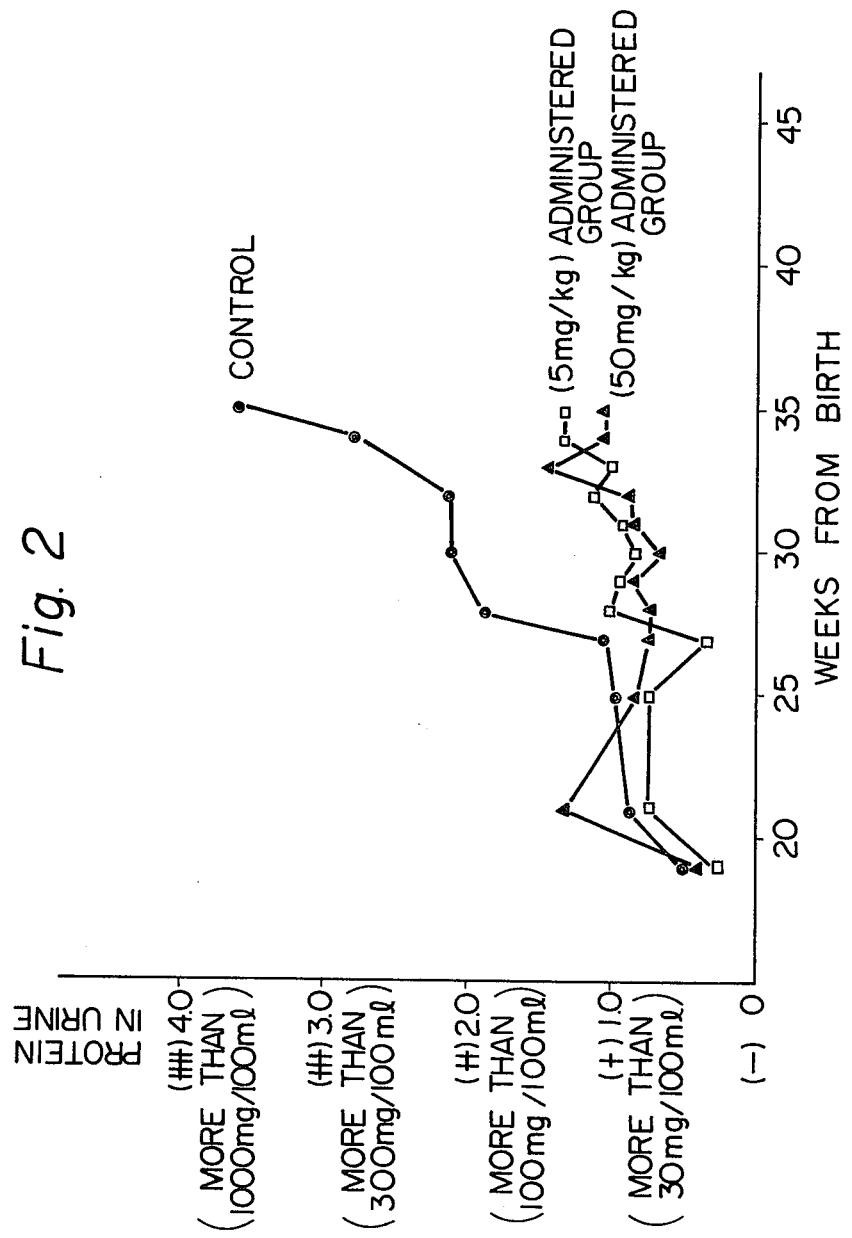
FIG. 2 is a graph showing the activity of the compound for treating a model of autoimmune disease.

Pharmacological activity of the test compound, disodium salt of N-2'-carboxyphenyl-4-chloroanthranilic acid, was studied by the use of glomerulonephritis of New Zealand Black/White $F_1$ female mice as a model of autoimmune disease. The test animals were divided into groups of 8 members each and orally administered with the test compound in a dose of 5 mg/kg or 50 mg/kg once a day from 8 week old. Development of the disease was evaluated by measuring the level of protein in urine with Combistix test paper (Ames Co., Inc.). It was confirmed that the evaluation by the test paper closely corresponds to the results of a quantitative analysis by a sulfosalicyclic acid method. Changes in average level of protein in urine each of the groups during a period of from 20 weeks old to 35 weeks old of the mice are shown in FIG. 2. FIG. 2 teaches that the level of protein in urine of the control significantly rose after around 27 weeks from birth, while all the groups administered with the test compound maintained a relatively steady level. Thus, the compound according to this invention significantly shows pharmacological activities to suppress autoimmune glomerulonephritis. Further, 3 mice among 8 mice of the control group were died from glomerulonephritis during the period of from 35 to 40 weeks from their birth, while there was no death in the groups to which the test compound had been administered.

EXPERIMENT 5

Antitumor Activity on Transplanted Tumor Cells (Sarcoma-180)

Figure 3:
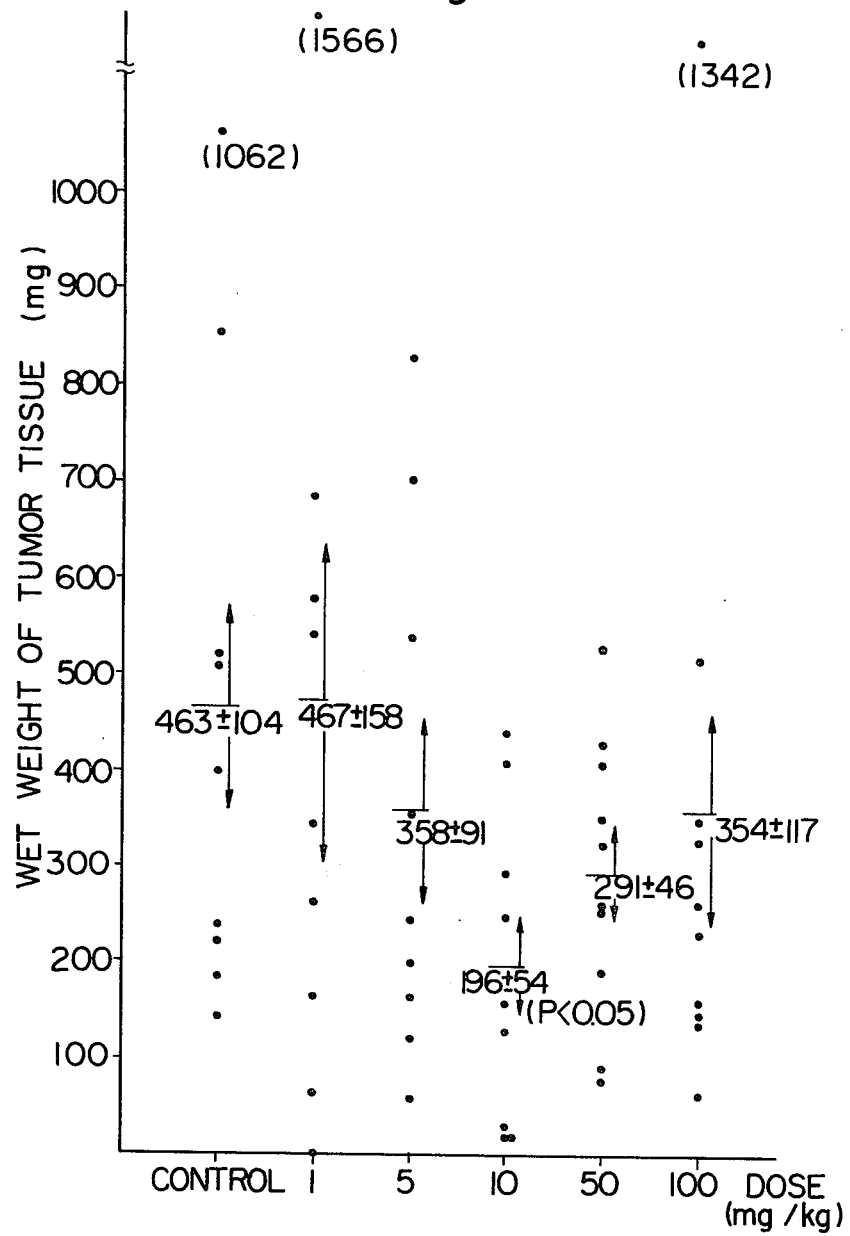
FIG. 3 is a graph showing the antitumor activity against transplanted tumor cells (Sarcoma-180)

For test animals, ddY strain male mice weighing 20 – 25 g were used dividing into groups of 9 or 10 members each. Each of the mice was subjected to transplantation of $10^6$ tumor cells (Sarcoma-180) at a portion of the root of a hind paw by subcutaneous injection to induce solid tumor. The test compound, disodium salt of N-2'-carboxyphenyl-4-chloroanthranilic acid, was orally administered once a day for 11 days from the day that transplantation was made. Fourteen days after the transplantation, the grown tumor tissue was taken out from each mouse and its wet weight was measured to evaluate antitumor activity of the test compound. The results are shown in FIG. 3. A 10 mg/kg dose of administration exhibits significant activity for suppression of tumor growth. The test compound does not suppress the growth of the same tumor cells in vitro, and it has no antitumor activity directly on the cells. For the reasons stated above, it is assumed that the activity of the test compound is based on host-mediated antitumor activity.

EXPERIMENT 6

Antitumor Activity to Transplanted Cancer Cells (AH-13)

As test animals, Donryu strain female rats (8 week old) which were divided into groups of 10 members each were used. Each rat was intraperitoneally administered with test compound, disodium salt of N-2'-carboxyphenyl-4-chloroanthranilic acid, once a day for 10 days from 16 days before the inoculation of the tumor cells disclosed hereinbelow. Sixteen days after the first administration of the test compound, each rat was intraperitoneally inoculated with $10^6$ tumor cells identified as AH-13 to induce cancer of abdominal dropsy. The average survival terms (days) of the rats after the inoculation of the tumor cells are shown in Table 6. It is clear that the 50 mg/kg administration of the test compound exhibits host-mediated antitumor activity.

Table 6

| Dose (mg/kg) | Survival Terms (days) | | | | | Average Survival Terms(days) | *T/C (%) |
|---|---|---|---|---|---|---|---|
| 200 | 7 | 7 | 7 | 6 | 7 | 6.9 | 97 |
|  | 7 | 8 | 6 | 7 |  |  |  |
| 100 | 7 | 6 | 6 | 7 | 7 | 7.3 | 103 |
|  | 6 | 6 | 13 |  |  |  |  |
| 50 | 7 | 13 | 11 | 15 | 11 | 11.6 | 163 |
|  | 17 | 8 | 10 | 12 | 12 |  |  |
| Control | 6 | 7 | 7 | 7 | 7 | 7.1 | 100 |
|  | 7 | 6 | 7 | 11 | 6 |  |  |

$$*T/C\ (\%) = \frac{\text{Average Survival Days (test group)}}{\text{Average Survival Days (control)}} \times 100$$

EXPERIMENT 7

Activity for Promoting Blastogenesis of Lymphocytes (Activation of Cellular Immunity)

In this Experiment, influence of the test compound disodium salt of N-2'-carboxyphenyl-4-chloroanthranilic acid on blastogenesis of lymphocytes was studied by the use of spleen cells and lymphonoid cells of mouse and rat. For in vitro test, $C_3H/He$ strain male mice and for in vivo Wistar-Imamichi strain male rats were used respectively. Concanavallin A manufactured by Sigma was used as the blastogenetic factor in the in vitro test and lymphocytes were cultured by the use of medium of RPMI 1640 manufactured by Grand Island Biological Co. The cultivation of the lymphocytes was carried out in the medium at 37° C in a 5% carbon dioxide atmosphere for about 48 hours and after the addition of 0.5 $\mu$Ci/ml of $^3$H-thymidine, the cells in the medium were incubated for 16 hours and then the lymphocytes were separated. The radioactivity of the separated cells was measured by a scintillation counter and the value was evaluated as an indicator of blastogenetic degree. For the in vivo test, the in vitro test was repeated except that each rat was orally administered with the test compound in a dose of 5 or 50 mg/kg. In this case, the rats administered with the test compound were divided into groups of 3 members each and the cells to be cultivated from the rats in each group were placed under the same cultivation conditions. The results of the experiments are shown in FIG. 4 (in vitro) and FIG. 5 (in vivo), respectively.

Figure 4:
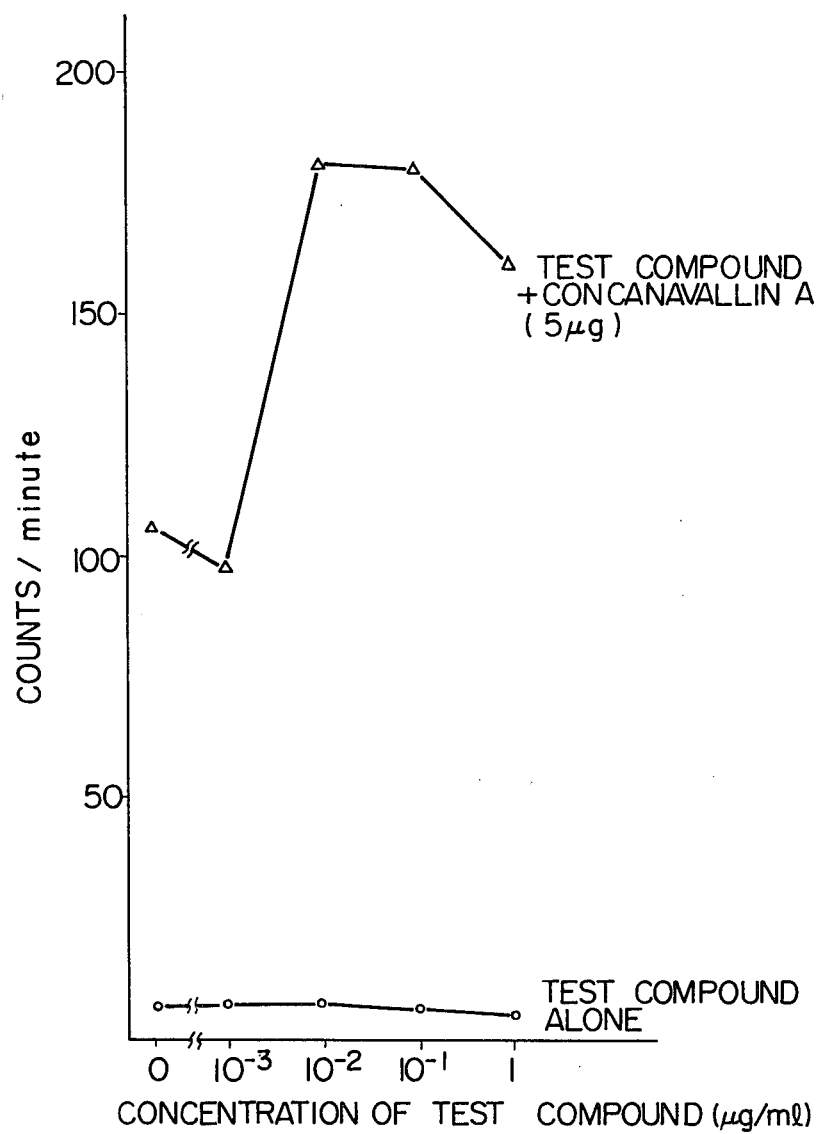
FIG. 4 is a graph showing the activity for promoting blastogenesis of lymphocytes (in vitro)
Figure 5:
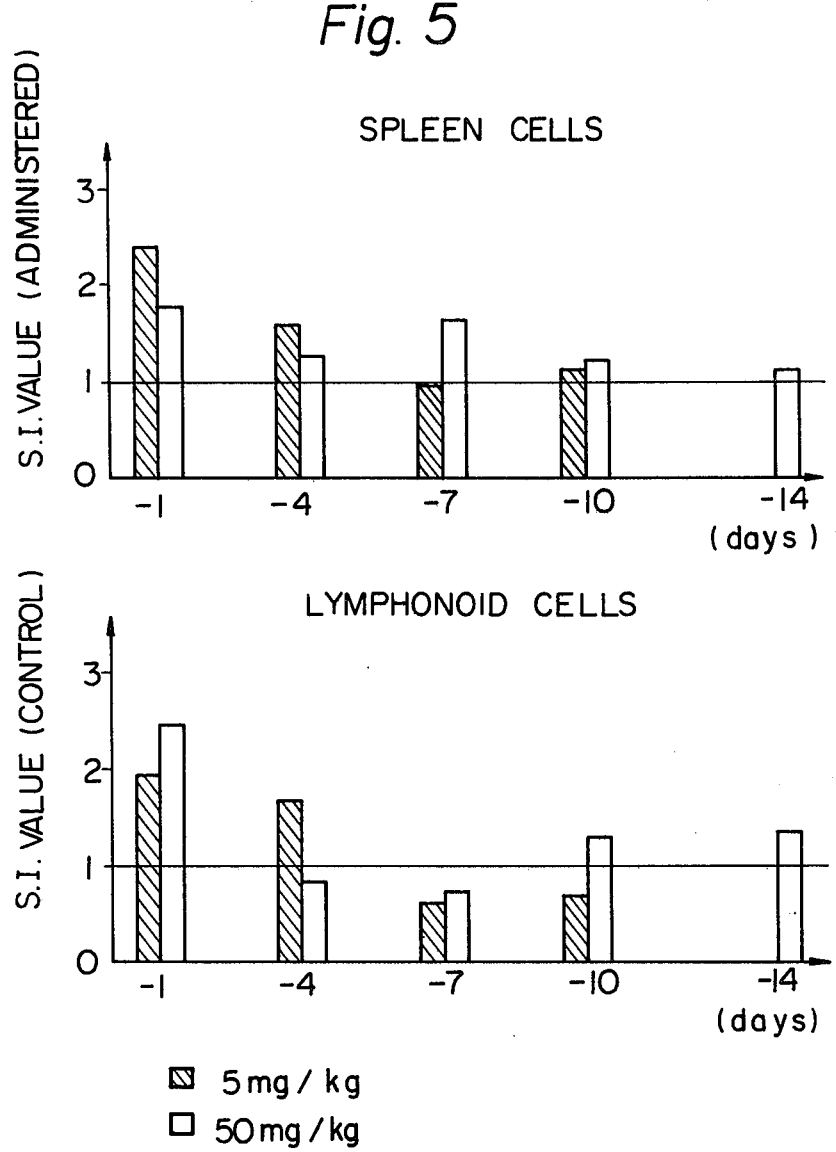
FIG. 5 is a graph showing the activity for promoting blastogenesis of lymphocytes (in vivo)

FIG. 4 clearly shows that the test compound of this invention in a concentration of from $10^{-1}$ to $10^{-2}$ $\mu$g/ml improved the activity of Concanavallin A. FIG. 5 shows that spleen cells and lymphocites of the rat administered with the test compound one day before the administration of Concanavallin A exhibit a degree of promotion (S.I. value) about twice as large as that of the control, and that the activity of Concanavallin A is increased to about double in comparison with that of the control. In the groups of rats or mice which were administered with the test compound four days before the administration or addition of Concanavallin A, the improvement of the activity was observed, but the degree of improvement of the activity was reduced as addition or administration of the test compound was earlier.

From the results mentioned above, it can be concluded that the test compound acts to improve blastogenesis of lymphocytes based on Concanavallin A not only in vitro but also in vivo and to potentiate cellular immunity.

EXPERIMENT 8

Activity for Potentiating Immune Reaction in Normal Animal (Activity for Protecting Bacterial Infection)

Sprague Dawley strain male rats weighing 200 - 220 g which were divided into 7 groups of 5 or 6 rats each were used as test animals.

The six groups were orally administered by one shot with the test compound, N-2'-carboxyphenyl-4-chloroanthranilic acid in a dose of 100 mg/kg on six different days, a day before the sensitization, on the date, a day after, two days after, three days after and four days after the sensitization with an antigen (SRBC: Sheep red blood cell). The SRBC was intraveneously injected in the rat through the tail vein in an amount of 1 ml as a 2% aqueous suspension. For control groups, a physiological saline solution was used in the same amount and in the same manner as those of the test groups on the day of sensitization.

Five days after the sensitization, the rats were sacrificed and the spleen of each of the rats was taken out and the blood was sampled.

The number of plaque forming cells and titers in blood were determined by the Jerne's plaque method and a hemolysing method, respectively.

The results are shown in Tables 7 and 8 below.

Table 7

| Increase in Number of Plaque Forming Cells | |
|---|---|
| Administration time (day) based on the sensitization | Number of plaque forming cell/$10^6$ cells |
| −1 | 93.2 ± 28.6 |
| 0 | 193.4 ± 26.6** (P<0.01) |
| +1 | 316.8 ± 38.2** (P<0.01) |
| +2 | 76.5 ± 16.3 |
| +3 | 101.0 ± 11.2 |
| +4 | 95.5 ± 35.3 |
| Control | 49.7 ± 16.0 |

Table 8

| Titer of Antibody in Blood | |
|---|---|
| Administration time (day) based on the sensitization | Final dilution showing hemolysis |
| −1 | $_2 9.5$ |
| 0 | $_2 10.8*$ ($P_{21\ 0.05}$) |
| +1 | $_2 13**$ (P<0.01) |
| +2 | $_2 9.5$ |
| +3 | $_2 9.8$ |
| +4 | $_2 8.7$ |
| Control | $_2 9.0$ |

\* significant
\*\* highly significant

Table 7 shows that there was a significant increase in the number of plaque forming cells when the rats were administered with the test compound on the date and a day after the sensitization. The increase reaches about six times as much as the value of the control group.

Table 8 shows that a significant increase in titers in blood was observed when the rats were administered with the test compound on the day and a day after the sensitization with SRBC.

EXPERIMENT 9

Activity for Recovering Immune Depletion (Activity for Protecting from Bacterial Infection)

Figure 6:
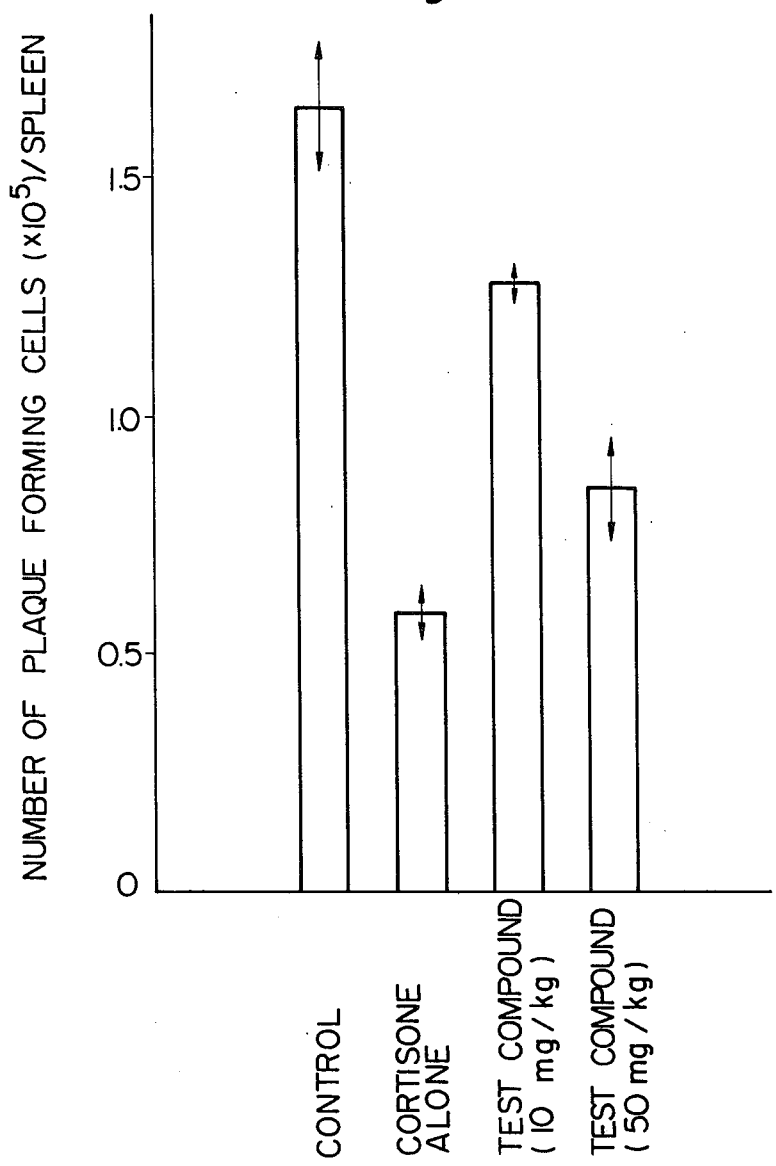
FIG. 6 is a graph showing the activity of the compound for recovering immune depletion.
Figure 7:
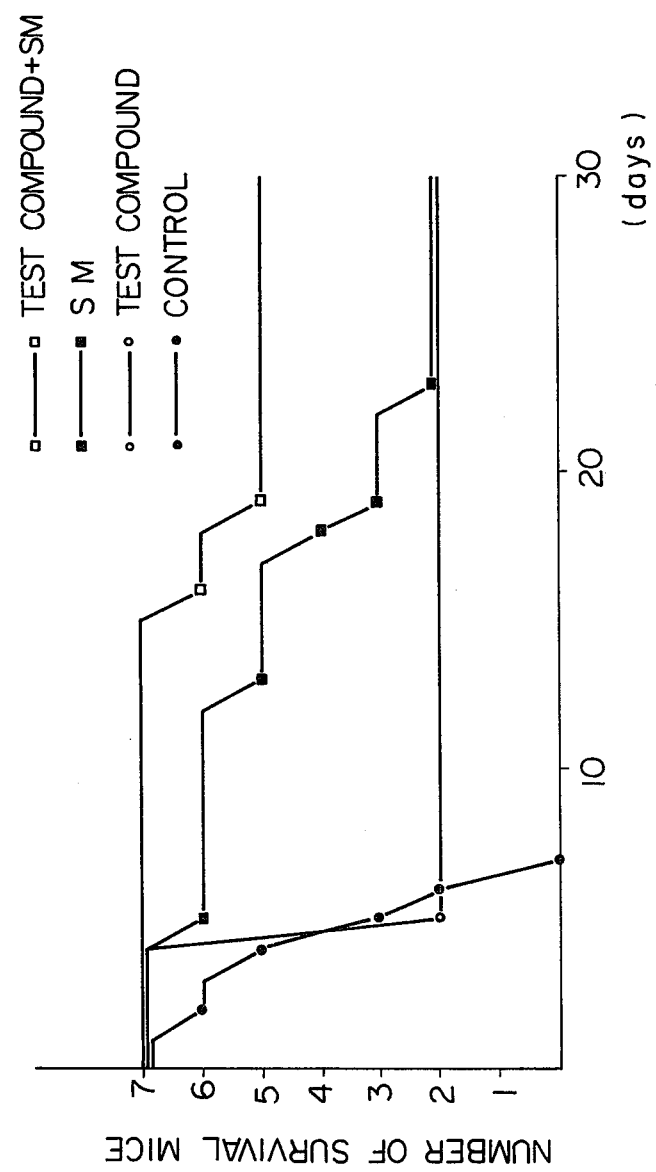
FIG. 7 is a graph showing activity for protecting infection by salmonellae.

As test animals, IV CS strain male mice (5 week old) were used by dividing them into groups of 5 members each. Each mouse was intraperitoneally administered with cortisone in a dose of 60 mg/kg once a day for 5 days. Three days after the first administration, the sensitization with an antigen, sheep red blood cell (SRBC), was made by injecting the antigen into the mouse through the tail vein. Each mouse was orally administered with the test compound, disodium salt of N-2'-carboxyphenyl-4-chloroanthranilic acid, a day after the sensitization. Five days after the sensitization, the number of plaque forming cells (PFC) in the spleen was measured in a usual manner. The results are shown in FIG. 6.

The number of PFC per spleen of the mouse in the group treated with cortisone alone was reduced to one third that of the control group without cortisone treatment. On the other hand, the number of PFC of the group administered with the test compound in a dose of 10 mg/kg was significantly increased. The results clearly show that the test compound acts to offset the activity of cortisone for depressing immunity and acts to recover the immune depletion.

Incidentally, titers of antibody in blood determined by a hemolysing method are shown in Table 9.

Table 9

| Treatment | Titer of Antibody* |
|---|---|
| Not treated | 12 |
| Cortisone | 3 |
| Cortisone + Test Compound (10 mg/kg) | $10^{10}$ |
| Cortisone + Test Compound (50 mg/kg) | $10^6$ |

* Titer of antibody in blood is indicated by a dilution degree of 50% hemolysis.

EXPERIMENT 10

Activity for Improving Bacteriocidal Ability in Neutrocyte (Activity for Protecting from Bacterial Infection)

As test animals, JW/CSK strain white male rabbits weighing 3.0 – 3.9 kg were used, dividing them into groups of 5 members each. Each rabbit was orally administered with the test compound, disodium salt of N-2'-carboxyphenyl-4-chloroanthranilic acid in a dose of 100 mg/kg, and 24 hours after the administration, neutrocyte in the blood of the peripheral vessels were reacted with nitrobluetetrazorium (NBT) and then the proportion of cells positive to formazan was measured by a microscope. As the control, the value obtained from the same animal just 3 days before the administration of the test compound was referred to. The results are shown in Table 10.

The results teach that the proportion of neutrocyte cells positive to formazan is significantly increased by the treatment with the test compound and that the test compound improves the bacteriocidal ability of neutrocyte.

Table 10

| Treatment | NBT Value * (%) |
|---|---|
| Before the treatment with Test Compound | 11.4 ± 1.8 |
| After the treatment with Test Compound | 33.3 ± 7.8* (P<0.05) |

* NBT Value is disclosed as "Average ± Standard Deviation".

EXPERIMENT 11

Activity for Protecting from Infection by *Bucillus Pyocyaneous*

As test animals, ddY strain male mice (5 week old) which were divided into groups of 7 members each were used. Each mouse was intraperitoneally inoculated with bucillus pyocyaneous, *Pseudomonas aeruginosa* Pa-II. The test compound, disodium salt of N-2'-carboxyphenyl-4-chloroanthranilic acid, was administered orally once a day in a dose of 2 mg/head 6, 5, 4 and 1 days before the inoculation, respectively, and the survival term of each mouse was observed for 54 hours after the inoculation. When $2 \times 10^5$ of the bacteria per head had been inoculated, activity of the test compound for protecting from the bacterial infection was observed. It is clear that the test compound acts to lower the bacillary toxin.

Table 11

| Number of Inoculated Bacteria (number/head) | Control | | Test Compound | |
|---|---|---|---|---|
| | Survival Term (hours) | Dead Animal Test Animal | Survival Terms (hours) | Dead Animal Test Animal |
| $2 \times 10^6$ | 22,24,24,24,24 26,26 | 7/7 | 24,24,24,24,24 29,29 | 7/7 |
| $2 \times 10^5$ | 45,45,45,45,48, 52,S | 6/7 | 46,S,S,S,S, S,S | 1/7 |
| $2 \times 10^4$ | 52,S,S,S,S, S,S | 1/7 | S,S,S,S,S, S,S | 0/7 |
| $LD_{50}$ (number/head) | $10^{4.8}$ | | $10^{5.7}$ | |

S: survival at 54 hours after the inoculation of bacteria

EXPERIMENT 12

Activity for Protecting from Infection by *Bucillus Pyocyaneous*

As test animals, ddY strain male mice (5 week old) which were divided into groups of 9 members each were used. Each mouse was intraperitoneally administered with $10^6$ *Pseudomonas aeruginosa* Pa-II, and 1.5 hours after the administeration, subcutaneously administered one shot of carbenicillin, an antibiotic. The test compound, disodium salt of N-2'-carboxyphenyl-4-chloroanthranilic acid, was orally administered once a day in a dose of 2 mg/head one and two days before the inoculation, respectively. The activity of the test compound was evaluated by observing the test animals for 54 hours after the inoculation. The results are shown in Table 12. The test results exhibit that the use of the antibiotic with the test compound gives improved bacteriocidal activity.

Table 12

| Dose of Carbenicillin (mg/head) | Number of Survival Animals / Number of Tested Animals | |
|---|---|---|
| | Carbenicillin | Carbenicillin + Test Compound |
| 40 | 9/9 | 9/9 |
| 20 | 2/9 | 7/9 |
| 10 | 0/9 | 4/9 |
| $ED_{50}$(mg/head) | 24.1 | 10.4 |

EXPERIMENT 13

Activity for Protecting from Infection by Salmonellae

As test animals, ddY strain male mice (5 week old) which were divided into groups of 7 members each were used. Each mouse was intraperitoneally inoculated with $10^5$ *Salmonella enteritidis* TO-1, and 3 hours after the inoculation, was subcutaneously administered one shot of streptomycine in a dose of 0.5 mg/head. The administration of the test compound, disodium salt of N-2'-carboxyphenyl-4-chloroanthranilic acid, was carried out with an oral dose of 2 mg/head orally on five different days, three days, two days and a day before the inoculation, on the date and a day after the inoculation. The results are shown in Table 7. The results exhibit that the use of the antibiotic with the test compound gives improved bacteriocidal activity.

EXPERIMENT 14

Activity for Treating Allergic Reaction (IgE Formation System) (Anti-Bronchinal Asthma Activity)

Figure 8:
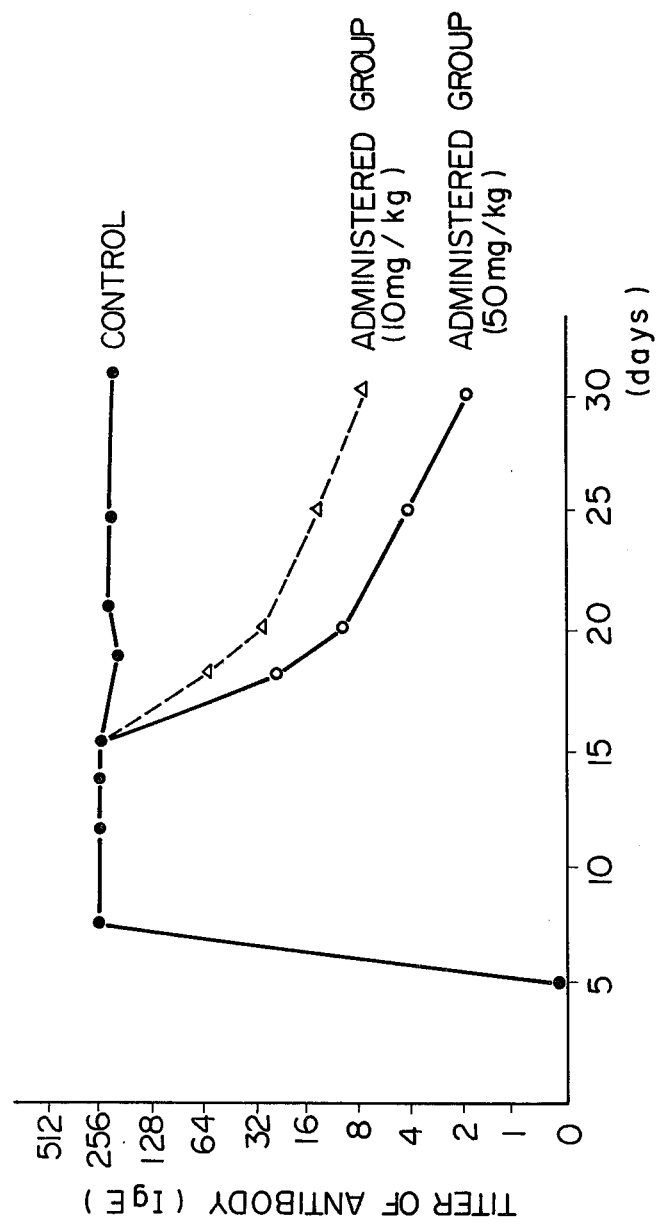
FIG. 8 is a graph showing activity of the compound for treating allergic reaction (IgE forming reaction).

As test animals, Wistar-Imamichi strain male rats (7 week old) which were divided into groups of 5 members each were used. Each rat was sensitized with the antigen, protein of ascaris which is bound with dinitrophenol radical (DNP-As) with the use of pertussis vaccine as an adjuvant by intracutaneous administration in the back of animal. Titer of IgE antibody was measured 3 hours after an intravenous injection of the antigen and a solution of Evans' Blue for inducing an immune reaction. The animal was irradiated with X-rays in a dose of 400 roentgen before the sensitization. The administration of the test compound was carried out orally once a day during a period of from 15 to 30 days from the sensitization. The titers of IgE antibody which were determined on the days 17, 20, 24 and 30 days after the sensitization by cutaneous reaction based on passive cataneous anaphylactic reaction are shown in FIG. 8. The results clearly exhibit that the test compound suppress the formation of IgE antibody and may be used for radical treatment of an allergic disease.

EXPERIMENT 15

Acute Toxicity

Acute toxicity of N-2'-carboxyphenyl-4-chloroanthranilic acid was determined using Wistar-Imamichi strain male and female rats (11 week old) as test animals. The test compound was orally administered as a suspension in a 5% gum arabi aqueous solution. The results are as follows.

| Sex of animal | LD$_{50}$ |
| --- | --- |
| male | 2,100 mg/kg |
| female | 2,600 mg/kg |

EXAMPLE 1

Isoamyl alcohol (250 ml), 2,4-dichlorobenzoic acid (12 g), anthranilic acid (17.5 g), potassium carbonate (18 g), powdery copper (500 mg) and a very small amount of iodine were charged into a 500 ml of round bottom, three-necked flask equipped with a mechanical stirrer and a condenser, and heated under reflux for 5 hours while stirring. The reaction mixture was allowed to cool to room temperature, followed by adding water (500 ml) and filtering it. The filtrate was condensed under reduced pressure while adding water to remove isoamyl alcohol, cooled on an ice-water bath and acidified with 6N hydrochloric acid to precipitate crystals. The crystals were suspended in ethanol, and the suspension was heated under reflux for 3 – 4 hours and cooled to precipitate crystals which were filtered off. The crystals were dissolved in tetrahydrofuran and active carbon was added to the solution followed by heating under reflux for 4 – 5 hours and, after the removal of the active carbon, by condensing under reduced pressure to remove tetrahydrofuran. The resulting residue were suspended again in methanol and the suspension was heated under reflux for 3 – 4 hours and allowed to cool to room temperature to precipitate crystals. The resulting crystals were separated by filtration to obtain 14 g of N-2'-carboxyphenyl-4-chloroanthranilic acid having a melting point above 306° C.

Analysis: Calcd. for $C_{14}H_{10}ClNO_4$: C, 57.64; H, 3.45; N, 4.80 (%); Found: C, 57.81; H, 3.39; N, 4.50 (%).

EXAMPLE 2

Example 1 was repeated except that 2,4-dichlorobenzoic acid and 5-methylanthranilic acid were used to obtain N-2'-carboxy-4'-methylphenyl-4-chloroanthranilic acid having a melting point between 316° – 318° C (decomposition). (Yield, 71.5%)

Calcd. for $C_{15}H_{12}ClNO_4$: C, 58.93; H, 3.95; N, 4.58 (%); Found: C, 58.98; H, 3.89; N, 4.58 (%).

EXAMPLE 3

Example 1 was repeated except that 2-chlorobenzoic acid and 5-methylanthranilic acid were used to obtain N-2'-carboxy-4'-methyl-phenylanthranilic acid having a melting point of 304° C. (Yield, 72%)

Analysis: Calcd. for $C_{15}H_{13}NO_4$: C, 66.41; H, 4.83; N, 5.16 (%); Found: C, 66.71; H, 4.78; N, 5.14 (%).

EXAMPLE 4

Example 1 was repeated except that 2,4-dichlorobenzoic acid and 3-methylanthranilic acid were used to obtain N-2'-carboxy-6'-methylphenyl-4-chloroanthranilic acid having a melting point between 302° – 304° C (decomposition) (Yield, 66%)

Analysis: Calcd. for $C_{15}H_{12}ClNO_4$: C, 58.93; H, 3.95; N, 4.58 (%); Found: C, 58.87; H, 4.04; N, 4.59 (%).

EXAMPLE 5

Example 1 was repeated except that 2,4-dichlorobenzoic acid and 4-chloroanthranilic acid were used to obtain N-2'-carboxy-5'-chlorophenyl-4-chloroanthranilic acid having a melting point of above 340° C. (Yield, 59%)

Analysis: Calcd. for $C_{14}H_9Cl_2NO_4$: C, 51.55; H, 2.78; N, 4.29 (%); Found: C, 51.56; H, 2.87; N, 4.27 (%)

EXAMPLE 6

Example 1 was repeated except that 2,4-dichlorobenzoic acid and 3,6-dimethylanthranilic acid were used to obtain N-2'-carboxy-3',6'-dimethylphenyl-4-chloroanthranilic acid having a melting point of 283° C. (Yield, 45%)

Analysis: Calcd. for $C_{16}H_{14}ClNO_4$: C, 60.10; H, 4.41; N, 4.38 (%); Found: C, 60.24; H, 4.42; N, 4.39 (%).

EXAMPLE 7

Example 1 was repeated except that 2-chlorobenzoic acid and 4-chloro-3-methylanthranilic acid were used to obtain N-2'-carboxy-5'-chloro-6'-methylphenylanthranilic acid having a melting point of 315° C. (Yield, 65%)

Analysis: Calcd. for $C_{15}H_{12}ClNO_4$: C, 58.93; H, 3.95; N, 4.58 (%); Found: C, 59.07; H, 3.97; N, 4.60 (%).

EXAMPLE 8

Example 1 was repeated except that 2,5-dichlorobenzoic acid and anthranilic acid were used to obtain N-2'-carboxyphenyl-5-chloroanthranilic acid having a melting point of 310° C. (Yield, 60%)

Analysis: Calcd. for $C_{14}H_{10}ClNO_4$: C, 57.64; H, 3.45; N, 4.80 (%); Found: C, 57.78; H, 3.52; N, 4.61 (%).

EXAMPLE 9

Isoamyl alcohol (50 ml), 2,4-dichlorobenzoic acid (2.4 g), anthranilic acid (3.5 g), anhydrous potassium carbonate (3.6 g) and powdery copper (0.4 g) were charged in 200 ml of an eggplant type flask and heated under reflux for 5 hours while stirring the mixture with a stirrer. After the completion of the reaction, the reaction mixture was cooled to room temperature and water was added to the mixture and the resulting mixture was filtered by suction. The filtrate was condensed under reduced pressure while adding water to it to remove isoamyl alcohol and acidified with 6N hydrochloric acid to precipitate crystals. The recovered crystals were dissolved in tetrahydrofuran and treated with active carbon and, after the removal of the active carbon, condensed to remove tetrahydrofuran. Methanol was added to the residue and the solution was heated under reflux and cooled to room temperature to obtain 1.1 g of N-2'-carboxyphenyl-4-chloroanthranilic acid as yellow amorphous substance. (m.p.: above 340° C) This product was the same as produced in Example 1.

EXAMPLE 10

N-2'-carboxyphenyl-4-chloroanthranilic acid (110 g) was dissolved in a solution of sodium hydroxide (30 g) in water (2 liters) and to the solution was added ethyl alcohol to obtain 88 g of sodium salt of N-2'-carboxyphenyl-4-chloroanthranilic acid having a melting point of 388° C (decomposition).

Analysis: Calcd. for $C_{14}H_8Na_2ClNO_4$: C, 50.09; H, 2.40; N, 4.17 (%); Found: C, 49.87; H, 2.26; N, 4.07 (%).

EXAMPLE 11

Pharmaceutical Preparation (a) Tablet

Pulverized N-2'-carboxyphenyl-4-chloroanthranilic acid (100 g) was thoroughly mixed with lactose (46 g), microcrystalline cellulose (27 g), corn starch (5 g) and magnesium stearate (2 g) and the mixture was formed into tablets with a tablet machine, each tablet being 8 mm in diameter and 180 mg in weight.

(b) Tablet

After being passed through a screen of 50 mesh, pulverized N-2'-carboxy-4'-methylphenyl-4-chloroanthranilic acid (200 g) was mixed with lactose (173 g) and calcium carboxymethylcellulose (20 g). The mixture was kneaded with a starch paste made of corn starch (4 g) in water and the resulting dough was granulated by a granulator and dried. The granules were passed through a screen of 14 mesh and, after the addition of and mixing with magnesium stearate (3 g), the mixture was formed into tablets, each tablet being 8 mm in diameter and 200 mg in weight.

(c) Powder

Lactose (149 g) and magnesium stearate (1 g) were thoroughly mixed with pulverized N-2'-carboxyphenyl-4-chloroanthranilic acid (250 g) to prepare powder.

(d) Capsules

Lactose (358 g) and magnesium stearate (2 g) were added to and thoroughly mixed with pulverized N-2'-carboxyphenyl-4-chloroanthranilic acid and hard gelatin capsules each weighing 65 mg were filled with 230 mg each of the mixture to form capsules.

(e) Granules

After being passed through a screen of 50 mesh, pulverized N-2'-carboxy-5'-chlorophenyl-4-chloroanthranilic acid (200 g) was mixed with lactose (173 g) and calcium carboxymethylcellulose (20 g), and the mixture was kneaded with a paste made of corn starch (4 g) in water. The resulting dough was granulated by an extrusion granulating machine, dried and passed through a screen of 14 mesh to form granules.

(f) Suspension

Crystalline cellulose (10 g) and sodium carboxymethylcellulose (0.75 g) were suspended in a solution (400 ml) of 200 g of sucrose in water to form a uniform suspension. Separately, N-2'-carboxyphenyl-4-chloroanthranilic acid (5 g) was pulverized together with sucrose (0.5 g) and water (20 ml) in a ball mill. The previously prepared suspension was added to the powder followed by water to make the total amount 500 ml and the mixture was stirred to form a uniform suspension.

(g) Parenteral Injection

Purified sodium salt of N-2'-carboxyphenyl-4-chloroanthranilic acid (10 g) and sodium chloride (9 g) were dissolved in distilled water for injection to make the total amount 1 leter. After the filtration of solution through a glass filter (G4) by suction, the solution was put in a 2 ml transparent ampule and, after the ampule was melt-sealed, subjected to heat sterilization at 100° C for 30 minutes.

We claim:

1. A process for preparing an aminobenzoic acid derivative represented by the formula

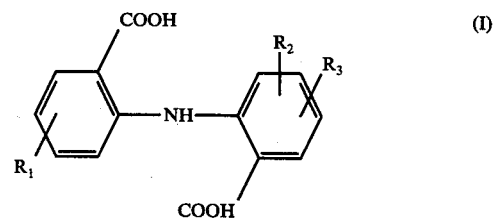

wherein $R_1$ is a hydrogen atom, or a halogen atom, $R_2$ and $R_3$ are a hydrogen atom, a halogen atom or an alkyl radical having 1 – 6 carbon atoms, provided that $R_1$, $R_2$ and $R_3$ are not simultaneously hydrogen atoms, which comprises reacting a 2-halogenobenzoic acid derivative represented by the formula

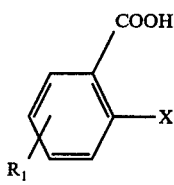

wherein $R_1$ is the same as defined above and X is a halogen atom with anthranilic acid or its derivative represented by the formula

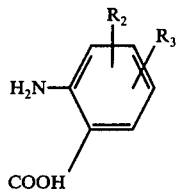

wherein $R_2$ and $R_3$ are the same as defined above, said reaction being carried out in the presence of an alkaline substance, copper, and iodine.

2. A pharmaceutical composition for treating disease from liver function disorder and immune depletion comprising an amount sufficient therefor of an aminobenzoic acid derivative of the formula

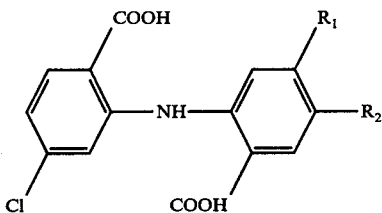

wherein $R_1$ and $R_2$ are independently hydrogen, methyl or chloro, provided that at least one of $R_1$ and $R_2$ is hydrogen, or an alkali salt thereof, and a pharmaceutically acceptable carrier and adjuvant.

3. A method for the treatment of disease from liver function disorder or immune depletion comprising administering to a mammal in need of such treatment an effective amount to treat said disease of a composition in accordance with claim 2.

4. A method in accordance with claim 3, wherein said administration is carried out by parenteral injection in a total amount of 0.5 – 1000 mg per day by one or more injections.

5. A method in accordance with claim 3, wherein said administration is in a total amount of 1 – 50 mg per day by one or more administrations.

6. N-2'-carboxyphenyl-4-chloroanthranilic acid.

7. N-2'-carboxy-4'-methylphenyl-4-chloroanthranilic acid.

8. N-2'-carboxy-5'-chlorophenyl-4-chloroanthranilic acid.

9. A process as set forth in claim 1 wherein said reaction is carried out at 80° – 200° C for 1 – 10 hours.

10. A process as set forth in claim 1 wherein the reaction is carried out at 120° – 150° C for 3 – 5 hours.

11. A process as set forth in claim 1 wherein said solvent is selected from the group consisting of isoamyl alcohol, dimethyl-sulfoxide, dimethylformamide, ethanol, butanol, n-amylalcohol, diethylene glycol dimethylether, and nitro benzene.

12. A process as set forth in claim 1 wherein the aminobenzoic acid derivative (III) is used in an amount of 1.2 – 2.0 mole based on a mole of the 2-halogenobenzoic acid derivative (II).

13. A process as set forth in claim 1 wherein said alkaline substance is potassium carbonate, sodium carbonate, or copper carbonate and is present in at least equimolar amount with compounds (II) and (III), and said copper is powdery copper, present in a small amount.

14. A process as set forth in claim 13 wherein said iodine is present in a small amount.

15. A pharmaceutical composition as set forth in claim 2 in oral administration from wherein the amount of the said composition is such that the use thereof realizes the administration of the aminobenzoic acid derivative in a total amount of 0.5 – 3000 mg per day by one or more times of administration.

16. A pharmaceutical composition as set forth in claim 15 wherein said composition is such that the use thereof realizes the administration of the aminobenzoic acid derivative in a total amount of 5 – 100 mg per day by one or more times of administration.

17. A pharmaceutical composition as set forth in claim 2 wherein said composition is such that the use thereof realizes the administration of the aminobenzoic acid derivative in a total amount of 1 – 50 mg per day by one or more times of administration.

18. A pharmaceutical composition as set forth in claim 2 wherein said aminobenzoic acid derivative is N-2'-carboxyphenyl-4-chloroanthranilic acid or an alkali salt thereof.

19. A pharmaceutical composition as set forth in claim 18 wherein said disease to be treated is rheumatic arthritis.

20. A method as set forth in claim 3 wherein said disease to be treated is autoimmune disease.

21. A method as set forth in claim 3 wherein said disease to be treated is bacterially infectious disease.

22. A method as set forth in claim 3 wherein said disease to be treated is asthma.

* * * * *